(12) United States Patent
Sato et al.

(10) Patent No.: US 9,260,499 B2
(45) Date of Patent: Feb. 16, 2016

(54) TUMOR ANTIGEN PEPTIDE AND USE THEREOF

(75) Inventors: Noriyuki Sato, Sapporo (JP); Tomohide Tsukahara, Sapporo (JP); Satoshi Kawaguchi, Sapporo (JP); Takuro Wada, Sapporo (JP)

(73) Assignees: SAPPORO MEDICAL UNIVERSITY, Sapporo-shi, Hokkaido (JP); SUMITOMO DAINTPPON PHARMA CO., LTD., Osaka-shi, Osaka (JP)

( * ) Notice: Subject to any disclaimer, the term of this patent is extended or adjusted under 35 U.S.C. 154(b) by 1030 days.

(21) Appl. No.: 13/125,044

(22) PCT Filed: Oct. 19, 2009

(86) PCT No.: PCT/JP2009/068013
§ 371 (c)(1),
(2), (4) Date: Apr. 19, 2011

(87) PCT Pub. No.: WO2010/047310
PCT Pub. Date: Apr. 29, 2010

(65) Prior Publication Data
US 2011/0200629 A1 Aug. 18, 2011

(30) Foreign Application Priority Data
Oct. 20, 2008 (JP) .................................. 2008-270078

(51) Int. Cl.
| | |
|---|---|
| C07K 7/06 | (2006.01) |
| C07H 21/00 | (2006.01) |
| C12N 5/10 | (2006.01) |
| G01N 33/574 | (2006.01) |
| C12Q 1/68 | (2006.01) |
| C07K 14/47 | (2006.01) |
| A61K 39/00 | (2006.01) |

(52) U.S. Cl.
CPC ......... *C07K 14/4748* (2013.01); *A61K 39/0011* (2013.01); *G01N 33/57407* (2013.01); *G01N 33/57438* (2013.01); *G01N 33/57484* (2013.01); *A61K 39/00* (2013.01); *G01N 2333/70539* (2013.01)

(58) Field of Classification Search
CPC ....................................................... C07K 7/06
USPC .......... 530/328; 536/23.1; 435/6.14, 7.23, 325
See application file for complete search history.

(56) References Cited

U.S. PATENT DOCUMENTS

| | | | |
|---|---|---|---|
| 6,083,513 A | 7/2000 | Grubhofer | |
| 7,171,311 B2 | 1/2007 | Dai et al. | |
| 7,700,108 B2 | 4/2010 | Sato et al. | |
| 2008/0014636 A1* | 1/2008 | Sato et al. | ................... 435/372.1 |

FOREIGN PATENT DOCUMENTS

| | | |
|---|---|---|
| EP | 1 136 555 A1 | 9/2001 |
| JP | 08-000985 A | 1/1996 |
| JP | 09-122476 A | 5/1997 |
| WO | WO-99/02546 A1 | 1/1999 |
| WO | WO-99/37660 A1 | 7/1999 |
| WO | WO-01/55437 A2 | 8/2001 |
| WO | WO-01/94629 A2 | 12/2001 |
| WO | WO-02/50103 A2 | 6/2002 |
| WO | WO-03/025138 A2 | 3/2003 |
| WO | WO-2004029248 A1 | 4/2004 |

OTHER PUBLICATIONS

Sato, N., et al., "Human PBF tumor antigen protein HLA-A24-binding peptide #22.", retrieved from EBI accession No. GSP:ADM57838, Jul. 1, 2004.
Sato, N., et al., "Human PBF tumor antigen protein HLA-A24-binding peptide #25.", retrieved from EBI accession No. GSP:ADM57841, Jul. 1, 2004.
Boeckle, S., et al., "A new cellular factor recognizes E2 binding sites of papillomaviruses which mediate transcriptional repression by E2.", retrieved from EBI accession No. UNIPROT:Q9H8N7, Sep. 13, 2005.
Strausberg, et al., Proc. Natl. Acad. Sci. USA., 2002 vol. 99, No. 26, pp. 16899-16903 (2002).
E. Gilboa et al., Cancer Immunol. Immunother, vol. 46, pp. 82-87 (1998).
M. Nakao et al., Cancer Research, vol. 55, Oct. 1, pp. 4248-4252 (1995).
M. Murakami et al., Cancer Research, vol. 59, Mar. 15, pp. 1184-1187 (1999).
C.L. Slingluff, Jr. et al., Clinical Cancer Research, vol. 7, pp. 3012-3024 (2001).
S.A. Rosenberg, Immunity, vol. 10, pp. 281-287 (1999).
H.G. Rammensee et al., Immunogenetics, vol. 41, pp. 178-228 (1995).
M. Herin et al., Int. J. Cancer, vol. 39, pp. 390-396 (1987).
D.D. Kharkevitch et al., Int. J. Cancer, vol. 58, pp. 317-323 (1994).
M. Gotoh et al., Int. J. Cancer, vol. 100, pp. 565-570 (2002).
V.Brichard et al., J. Exp. Med. vol. 178, pp. 489-495 (1993).

(Continued)

*Primary Examiner* — Yan Xiao
(74) *Attorney, Agent, or Firm* — Birch, Stewart, Kolasch & Birch, LLP

(57) ABSTRACT

Disclosed is a peptide consisting of the identical amino acid sequence or a substantially identical amino acid sequence to the amino acid sequence depicted in SEQ ID NO:4, wherein the peptide binds to an HLA antigen and is recognized by cytotoxic T cells. The peptide of the present invention can be used in vivo or in vitro as an agent for inducing CTL, that is, cancer vaccine, and exerts therapeutic or ameliorating effects on tumors such as osteosarcoma, renal cancer, and others. The peptide of the present invention is also useful as a tumor marker directed to tumors such as sarcoma, renal cancer, and others.

16 Claims, 2 Drawing Sheets

(56) References Cited

OTHER PUBLICATIONS

A.B.H. Bakker et al., J. Exp. Med., vol. 179, pp. 1005-1009 (1994).
B. Fisk et al., J. Exp. Med. vol. 181, pp. 2109-2117 (1995).
D. Boczkowski et al., J. Exp. Med., vol. 184, pp. 465-472 (1996).
M.B. Bloom et al., J. Exp. Med., vol. 185, No. 3, pp. 453-459 (1997).
S. Shichijo et al., J. Exp. Med., vol. 187, No. 3, pp. 277-288 (1998).
S.A. Rosenberg et al., Journal of the National Cancer Institute, vol. 86, No. 15, pp. 1159-1166 (1994).
K.Y. Tsang et al., Journal of the National Cancer Institute, vol. 87, No. 13, pp. 982-990 (1995).
P. Correale et al., Journal of the National Cancer Institute, vol. 89, No. 4, Feb. 19, 1997, pp. 293-300.
W.H. Hildebrand et al., Journal of Immunology, vol. 148, No. 4, pp. 1155-1162 (1992).
R.T. Kubo et al., Journal of Immunology, vol. 152, pp. 3913-3924 (1994).
L. Rivoltini et al., Journal of Immunology, vol. 154, pp. 2257-2265 (1995).
A. Kondo et al., Journal of Immunology, vol. 155, pp. 4307-4312 (1995).
T. Sudo et al., Journal of Immunology, vol. 155, pp. 4749-4756 (1995).
V. Tsai et al., Journal of Immunology, vol. 158, pp. 1796-1802 (1997).
J. Alexander et al., Journal of Immunology, vol. 159, pp. 4753-4761 (1997).
P. Correale et al., Journal of Immunology, vol. 161, pp. 3186-3194 (1998).
L.H. Butterfield et al., Journal of Immunology, vol. 161, pp. 5607-5613 (1998).
G.Y. Ishioka et al., Journal of Immunology, vol. 162, 1999, pp. 3915-3925.
E.A. Walter et al., New England Journal of Medicine, vol. 333, No. 16, pp. 1038-1044 (1995).
J.D. Thompson et al., Nucleic Acids Research, vol. 22, No. 22, pp. 4673-4680 (1994).
Y. Kawakami et al., Proc. Natl. Acad. Sci. USA, vol. 91, pp. 3515-3519 (1994).
J.D. Altman et al., Science, vol. 274, pp. 94-96 (1996).
S. Boeckle et al., Virology, vol. 293, pp. 103-117 (2002).
T. Tsukahara et al., Cancer Research, vol. 64, No. 15, pp. 5442-5448 (2004).
T. Tsukahara et al., "Prognostic Impact and Immunogenicity of a Novel Osteosarcoma Antigen, Papillomavirus Binding Factor, in Patients with Osteosarcoma," Cancer Science, vol. 99, No. 2, pp. 368-375 (2008).
Konya et al., J. Gen. Virol., vol. 78, pp. 2615-2620 (1997).
May et al., J. Gen. Virol., vol. 72, pp. 2989-2997 (1991).
Wu, An-Hua et al., "Identification of EGFRvIII-derived CTL Epitopes Restricted by HLA A0201 for Dendritic Cell Based Immunotherapy of Gliomas," Journal of Neuro-Oncology, vol. 76, pp. 23-30, (2006).
Tsukahara, Tomohide et al., "HLA-A*0201-restricted CTL Epitope of a Novel Osteosarcoma Antigen, Papillomavirus Binding Factor," Journal of Translational Medicine, vol. 7, No. 44, pp. 1-10, 2009 and supplemental online Table.
Amrolia, Persis J. et al., "Allorestricted Cytotoxic T Cells for Human CD45 Show Potent Antileukemic Activity," Blood, vol. 101, No. 3, pp. 1007-1014, (2002).
Pinilla-Ibarz, Javier et al., "Synthetic Peptide Analogs Derived from BCR/ABL Fusion Proteins and the Induction of Heteroclitic Human T-cell Responses," Hematologica/The Hemotology Journal, vol. 90, No. 10, pp. 1324-1332, (2005).
Office Action dated Aug. 13, 2012 in copending U.S. Appl. No. 12/702,274.
Tsukahara, T. et al., "Analysis of function of osteosarcoma cell line and cytotoxic T cell (CTL) clone against osteosarcoma for the purpose of identifying osteosarcoma antigen," Record of Meeting of the Japanese Society for Immunology held on Oct. 31, 2001, 2-C-W11-43-P, p. 169.
Shedlock et al., "DNA vaccination: antigen presentation and the induction of immunity," Journal of Leukocyte Biology, vol. 68, pp. 793-806, Dec. 2000.
Staveley-O'Carroll et al.,"Induction of antigen-specific T-cell anergy: An early event in the course of tumor progression," Proceedings of the National Academy of Sciences, vol. 95, pp. 1178-1183, Feb. 1998.
Bodey et al., "Failure of Cancer Vaccines: The Significant Limitations of this Approach to Immunotherapy," Anticancer Research, vol. 20, pp. 2665-2676, 2000.
Radoja et al., "Cancer-induced Defective Crytotoxic T Lymphocyte Effector Function: Another Mechanism How Antigenic Tumors Escape Immune-mediated Killing," Molecular Medicine, vol. 6, No. 6, pp. 465-479, 2000.
US Office Action issued in co-pending U.S. Appl. No. 12/702,274.
Tsukahara et al., "Prognostic Impact and Immunogenicity of a Novel Osteosarcoma Antigen, Papillomavirus Binding Factor, in Patients with Osteosarcoma", Cancer Sci., vol. 99, No. 2 (2008) pp. 368-375.

* cited by examiner

TUMOR ANTIGEN PEPTIDE AND USE THEREOF

The present application is the national stage application of the International Application PCT/JP2009/068013, filed Oct. 19, 2009. This application also claims priority under 35, USC §119 (a)-(d) of Japanese Application 2008-270078, filed Oct. 20, 2008.

TECHNICAL FIELD

The present invention relates to a tumor antigen peptide. More specifically, the present invention relates to use of a fragment peptide of a tumor antigen protein (papillomavirus binding factor, PBF) and a gene thereof in the field of cancer immunity.

BACKGROUND ART

Cellular immunity, especially cytotoxic T cells (hereinafter referred to as CTLs), play an important role in eliminating tumor cells, virally infected cells, etc., from the living body. CTLs recognize a complex of an antigenic peptide (tumor antigen peptide) on a tumor cell and an MHC (Major Histocompatibility Complex) class I antigen, which is referred to as HLA antigen in the case of humans, and attack and kill the tumor cells.

Tumor antigen peptides are generated by intracellular degradation of proteins specific for tumors (i.e., tumor antigen proteins) by proteases, after the proteins are synthesized in cells. The resulting tumor-antigen peptide binds to an MHC class I antigen (HLA antigen) in the endoplasmic reticulum to form a complex, which is transported to the cell surface and presented as an antigen. The tumor-specific CTLs, when these recognize the complex presented as an antigen, exhibit anti-tumor effects through the cytotoxic actions or production of lymphokines. The elucidation of a series of these actions has allowed therapies which boost tumor-specific CTLs in patients with tumors by using tumor antigen proteins or peptides as so-called cancer immunotherapeutic agents (cancer vaccines).

Tumor antigen proteins include, as representative examples, ones listed in Table 1 of Non-Patent Document 1. Further, a papillomavirus binding factor (PBF) which recognizes the E2 binding site of papillomaviruses (GenBank Database Accession No. AF263928, SEQ ID NO:2) was reported as a tumor antigen protein applicable to cancers (tumors) including sarcomas (e.g., osteosarcoma) (patent document 1). In addition, tumor antigen peptides binding to the HLA-A24 or HLA-B55 antigen were identified. However, PBF-derived tumor-antigen peptides which bind to an HLA-A2 antigen have not been found yet.

[Non-Patent Document 1] Immunity, vol. 10:281, 1999
[Patent Document 1] International Publication No. WO 04/029248

These documents are incorporated herein by reference.

DISCLOSURE OF THE INVENTION

Problems to be Solved by the Invention

An object of the present invention is to provide, for example, use of a fragment peptide of a tumor antigen protein:PBF, which binds to an HLA-A2 antigen, and a gene thereof in the field of cancer immunity.

Means for Solving the Problems

As a result of dedicated research, the present inventors have found a fragment peptide of a papillomavirus binding factor (PBF) registered as GenBank Accession No. AF263928 (SEQ ID NO:2), which is a tumor antigen peptide binding to an HLA-A2 antigen.

The present inventors have demonstrated that the tumor antigen peptide can be used as an agent for inducing CTLs in vivo or in vitro, that is, cancer vaccine, and exerts therapeutic or ameliorating effects on tumors such as osteosarcoma, renal cancer, and others. The tumor antigen peptide is also useful as a tumor marker for tumors such as sarcoma, renal cancer, and others.

Therefore, the present invention includes:

(1) A peptide consisting of the amino acid sequence, which is identical or substantially identical to the amino acid sequence of SEQ ID NO:4, wherein the peptide binds to an HLA antigen and is recognized by cytotoxic T-cells (hereinafter referred to as "CTLs").
(2) The peptide according to (1), wherein the HLA antigen is HLA-A2.
(3) The peptide according to (2), consisting of the amino acid sequence of SEQ ID NO:4 or an amino acid sequence comprising a substitution of an amino acid residue in the amino acid sequence of SEQ ID NO:4 wherein an amino acid residue at position 2 of SEQ ID NO:4 is substituted by methionine, valine, isoleucine or glutamine, or the amino acid residue at the C-terminal of SEQ ID NO:4 is substituted by leucine.
(4) A peptide consisting of the amino acid sequence of SEQ ID NO:4.
(5) An agent for inducing CTL comprising as an active ingredient the peptide according to any one of (1) to (4).
(6) An agent for inducing CTL comprising a nucleic acid encoding a peptide consisting of the amino acid sequence which is identical or substantially identical to the amino acid sequence of SEQ ID NO:4
(7) The agent for inducing CTL according to (6), wherein the polynucleotide is a polynucleotide consisting of the sequence of SEQ ID NO:3.
(8) A nucleic acid consisting of a polynucleotide encoding the peptide according to any one of (1) to (4).
(9) An agent for inducing CTL which comprises the nucleic acid according to (8).
(10) A method of producing an antigen presenting cell, wherein the method is characterized by contacting in vitro one of the following:
(a) the peptide according to any one of (1) to (4), or
(b) a nucleic acid comprising a polynucleotide encoding the peptide of (a), with a cell having antigen-presenting capability.
(11) An antigen presenting cell produced by the method according to (10).
(12) A method of inducing a CTL, wherein the method is characterized by contacting in vitro one of the following:
(a) the peptide according to any one of (1) to (3),
(b) a nucleic acid comprising a polynucleotide encoding the peptide of (a), with a peripheral blood lymphocyte.
(13) A CTL induced by the method according to (12).
(14) An antibody which specifically binds to the peptide according to any one of (1) to (4).
(15) A tumor marker which comprises a polynucleotide encoding a peptide consisting of an amino acid sequence which is identical or a substantially identical to the amino acid sequence of SEQ ID NO:4, or a polynucleotide complementary to the polynucleotide.
(16) The tumor marker according to (15), wherein the tumor marker comprises a polynucleotide comprising the sequence of SEQ ID NO:3, or a polynucleotide complementary to the polynucleotide.

(17) A tumor marker which consists of a polypeptide consisting of an amino acid sequence which is identical or a substantially identical to the amino acid sequence of SEQ ID NO:4.
(18) The tumor marker according to (17), wherein the tumor marker consists of a polypeptide which is identical to the amino acid sequence of SEQ ID NO:4.
(19) A tumor marker which consists of an antibody against a peptide consisting of the amino acid sequence which is identical or a substantially identical to the amino acid sequence of SEQ ID NO:4, or the antibody according to (14).
(20) The tumor marker according to (19), wherein the tumor marker consists of an antibody against a peptide consisting of the amino acid sequence of SEQ ID NO:4.
(21) An HLA tetramer which comprises the peptide according to any one of (1) to (4) and an HLA antigen.
(22) A tumor marker which consists of the HLA tetramer according to (21).
(23) The tumor marker according to any one of (15) to (20) and (22), wherein the tumor is sarcoma or renal cancer.
(24) An agent for the diagnosis of a tumor, wherein the agent comprises the tumor marker according to any one of (15) to (20), (22), and (24).

Effects of the Invention

The present invention provides, for example, a tumor antigen peptide and a gene thereof which are useful as an agent for inducing CTL. The agent for inducing CTL provided by the present invention are useful, for example, as a therapeutic agent for sarcoma, renal cancer, and others.

BEST MODE FOR CARRYING OUT THE INVENTION

Figure 1:
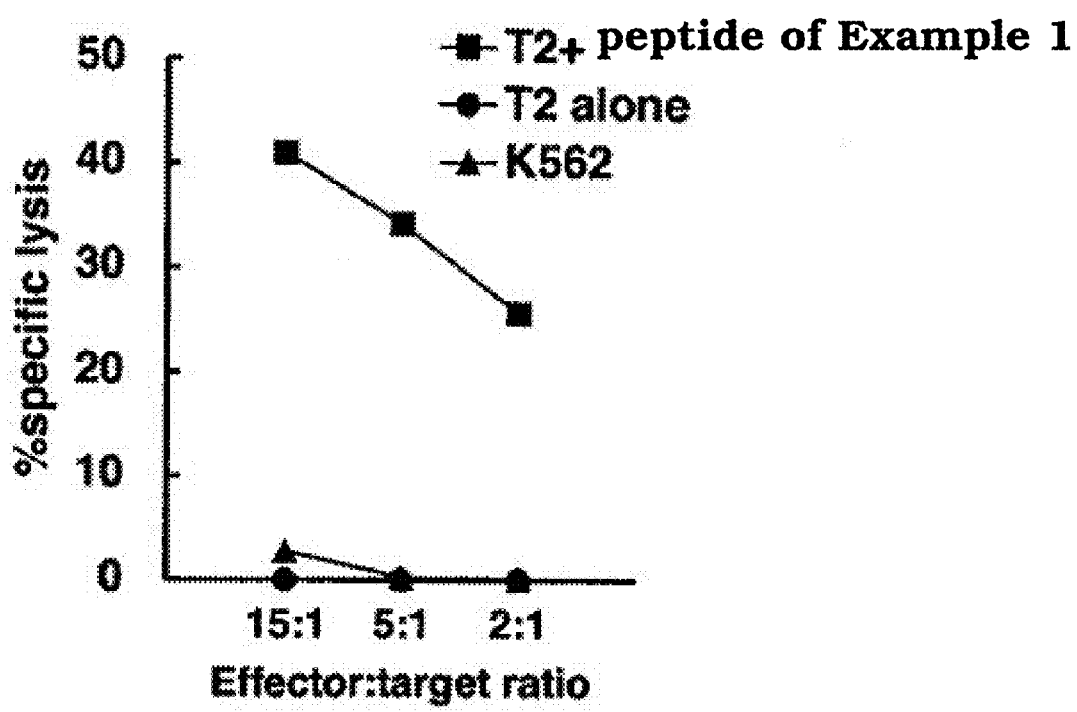
FIG. 1 is a graph showing the peptide-specific cytotoxic activity of CTL5A9. The ordinate indicates the cytotoxic activity and the abscissa indicates the ratio of the number of CTL5A9 cells (effector) and the number of target cells.

1) Peptides Provided by the Present Invention
A peptide provided by the present invention, which may be referred to hereinafter as "a peptide of the present invention" is a tumor antigen peptide comprising an amino acid sequence which is identical or a substantially identical to the amino acid sequence of SEQ ID NO:4, and a peptide of the present invention is a peptide fragment of the above-described PBF protein, and has the activity of binding to an HLA antigen, preferably an HLA-A2 antigen, whereby the peptide is recognized by CTLs.
As used herein, "amino acid sequence which is substantially identical" refers to any amino acid sequence without limitation, as long as a peptide consisting of "amino acid sequence which is substantially identical" exerts an activity similar to a tumor antigen peptide consisting of the amino acid sequence of SEQ ID NO:4. For example, an amino acid sequence which is substantially identical can include an amino acid sequence having a substitution of methionine, valine, isoleucine, or glutamine for the amino acid at the second position, or a substitution of leucine for the amino acid at the C-terminal in the amino acid sequence of SEQ ID NO:4. In this connection, regarding HLAs of the HLA-A2 type (e.g., HLA-A0201, -A0204, -A0205, -A0206, and -A0207), a regular pattern of the sequence (i.e., motif) of presented antigen peptides is known, as shown in Table 1 below (Immunogenetics, 41, p. 178, 1995; and J. Immunol., 155, p. 4749, 1995, which are incorporated herein by reference).

TABLE 1

| Type of HLA-A2 | 2nd amino acid from the N-terminal | C-terminal amino acid |
| --- | --- | --- |
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

A peptide of the present invention may be a peptide derived from a natural product (e.g., the above-described PBF protein) or a synthesized peptide. The peptide preferably has a length of not more than 11 amino acids, more preferably 9 amino acids.

A peptide of the present invention can be synthesized in accordance with methods used in conventional peptide chemistry. Such known methods include, for example, methods described in the literature: Peptide Synthesis, Interscience, New York, 1966; The Proteins, Vol. 2, Academic Press Inc., New York, 1976; PEPUCHIDO GOSEI [Peptide Synthesis], Maruzen Co., Ltd., 1975; PEPUCHIDO GOSEI NO KISO TO ZIKKEN [Basics and Experiments for Peptide Synthesis], Maruzen Co., Ltd., 1985; IYAKUHIN NO KAIHATSU, ZOKU [Developments of Pharmaceuticals, 2nd Series], vol. 14: PEPUCHIDO GOSEI [Peptide Synthesis], Hirokawa Publishing Co., 1991, which are incorporated herein by reference.

It is possible to determine whether or not a peptide of the present invention has an activity as a tumor antigen peptide, by assaying whether or not a complex of the peptide with an HLA-A2 antigen is recognized by CTLs.

A particular method, for example, includes the method described in J. Immunol., 154, p. 2257, 1995, which is incorporated herein by reference. According to the method, an induction of CTLs which specifically recognize HLA-A2 antigen-positive cells pulsed with the candidate peptide may be confirmed when peripheral blood lymphocytes are isolated from a human who is positive for an HLA-A2 antigen and stimulated in vitro by the addition of a candidate peptide. In this case, whether or not such CTLs have been induced may be determined, for example, by measuring the amount of various cytokines (e.g., IFN-γ) produced by the CTLs in response to antigen peptide-presenting cells using ELISA or the like. Alternatively, the induction of CTLs may also be determined by methods of measuring the cytotoxic activity of CTLs against antigen peptide-presenting cells labeled with $^{51}Cr$ ($^{51}Cr$ release assay, Int. J. Cancer, 58, p. 317, 1994, which is incorporated herein by reference).

As for the above-described CTLs, in addition to CTLs prepared by stimulating human peripheral blood lymphocytes with a peptide, CTLs, which are established by methods described, for example, in Int. J. Cancer, 39, 390-396, 1987; and N. Eng. J. Med, 333, 1038-1044, 1995 (which are incorporated herein by reference), may be used.

The in vivo activity of a peptide of the present invention can be determined by an assay using an animal model for human (WO 02/47474, and Int J. Cancer, 100, 565-570 (2002), which are incorporated herein by reference).

In addition, a peptide of the present invention includes a peptide in which a plurality of epitopes including a peptide of the present invention are coupled (i.e., polyepitope peptide).

Therefore, a polyepitope peptide which has a CTL inducing activity can also be a particular example of a peptide of the present invention.

As used herein, a polyepitope peptide is defined as a peptide, which is (i) a particular peptide in which a peptide of the present invention and any plurality of other PBF-derived CTL epitopes (tumor antigen peptides) are coupled; (ii) a peptide in which a peptide of the present invention and a helper epitope are coupled; or (iii) a peptide in which a peptide of the present invention, any plurality of other PBF-derived CTL epitopes (tumor antigen peptides), and further a helper epitope are coupled, and which undergoes intracellular processing in antigen presenting cells so that the resulting tumor antigen peptides presented on the antigen presenting cells induce CTLs.

In the case where an epitope to be linked to a peptide of the present invention is a helper epitope, the available helper epitope includes HBVc 128-140 derived from hepatitis B virus and TT947-967 derived from tetanus toxin, as described above. The helper epitope, for example, has a length of 13 to 30 amino acids or so, preferably 13 to 17 amino acids or so.

The peptide, in which plural epitopes are coupled (polyepitope peptide) as described above, can be prepared by a conventional method for peptide synthesis as described above. Alternatively, the polyepitope peptide, in which the plural epitopes are coupled as described above, can also be prepared using conventional DNA synthesis and genetic engineering procedures, based on the sequence information of a polynucleotide encoding the polyepitope peptide. In other words, a polyepitope peptide may be prepared by inserting the polynucleotide into a well-known expression vector; transforming a host cell with the resultant recombinant expression vector; culturing the obtained transformant; and collecting from the culture the desired polyepitope peptides in which plural epitopes are coupled. As mentioned previously, the procedure may be carried out, for example, in accordance with methods described in the literature: Molecular Cloning, T. Maniatis et al., CSH Laboratory (1983); and DNA Cloning, D M. Glover, IRL PRESS (1985), which is incorporated herein by reference.

The activity for inducing CTLs of the prepared polyepitope peptide, in which plural epitopes are coupled, may be determined, for example, by the above-mentioned in vitro assays of the peptide or in vivo assays of the peptide using an animal model for human described in WO 02/47474 and Int J. Cancer, 100, 565-570 (2002), which are incorporated herein by reference.

2) A Nucleic Acid of the Present Invention

A nucleic acid provided by the present invention, which may be referred to hereinafter as "a nucleic acid of the present invention" comprises a polynucleotide encoding the above-described peptide of the present invention.

A nucleic acid of the present invention may be either of a cDNA, mRNA, or cRNA from various cells or various tissues such as osteosarcoma, renal cancers and others. Alternatively, a nucleic acid of the present invention may be a synthetic DNA. Also, a nucleic acid of the present invention may be in the form of either single or double strands. For example, a nucleic acid of the present invention includes:

(a) a polynucleotide consisting of the nucleic acid sequence of SEQ ID NO:3;

(b) a polynucleotide consisting of a nucleic acid sequence encoding the amino acid sequence of SEQ ID NO:4; and (c) a polynucleotide consisting of a nucleic acid sequence encoding an amino acid sequence which is substantially identical to the amino acid sequence of SEQ ID NO:4.

A nucleic acid comprising the polynucleotide of the present invention can take the form of either single or double strands. When a polynucleotide of the present invention is a double strand, it can be inserted into an expression vector to make a recombinant expression vector for expressing a peptide of the present invention. Therefore, a recombinant expression vector which is obtained by inserting a double-stranded polynucleotide of the present invention into an expression vector is encompassed by a nucleic acid of the present invention.

An expression vector which is used herein can be adequately selected, depending on hosts to be used, its purposes for use, and others, and includes plasmids, phage vectors, viral vectors, and the like.

In the case where host is *Escherichia coli*, for example, a vector includes plasmid vectors such as pUC118, pUC119, pBR322, and pCR3; and phage vectors such as λZAPII and λgt11. In the case where host is yeast, a vector includes pYES2, pYEUra3, and the like. In the case where host is an insect cell, a vector includes pAcSGH is NT-A and the like. In the case where host is an animal cell, a vector includes plasmid vectors such as pCEP4, pKCR, pCDM8, pGL2, pcDNA3.1, pRc/RSV, and pRc/CMV; and viral vectors such as retroviral vectors, adenoviral vectors, and adeno-associated viral vectors.

The above-described vectors may comprise various elements such as an expression-inducible promoter, a gene encoding a signal sequence, a gene encoding a selective marker, and a terminator, if needed.

In addition, vectors may have an added sequence which expresses as a fusion protein with thioredoxin, His-tag, GST (glutathione S-transferase), or the like, so as to facilitate isolation and purification of it. In this connection, vectors for GST fusion proteins (e.g., pGEX4T) having an appropriate promoter operable in host cells (e.g., lac, tac, trc, trp, CMV, SV40 early promoter), vectors having a tag sequences such as Myc and His, (e.g., pcDNA3.1/Myc-His), or vectors expressing a fusion protein with thioredoxin and His-tag (pET32a) can be used.

Hosts can be transformed with an expression vector produced as described above, thereby generating transformed cells containing the expression vector.

Hosts which can be used herein include *Escherichia coli*, yeast, insect cells, animal cells, and others. *Escherichia coli* includes *E. coli* K-12 strains such as HB101, C600, JM109, DH5α, AD494(DE3), etc. Yeast includes *Saccharomyces cerevisiae*, etc. Animal cells include L929 cells, BALB/c3T3 cells, C127 cells, CHO cells, COS cells, Vero cells, Hela cells, 293-EBNA cells, etc. Insect cells include sf9 cells, etc.

As methods for introducing an expression vector into host cells, a conventional method which is adapted to the respective host cell as described above may be used. For example, such methods include a method using calcium phosphate, DEAE-dextran, an electroporation method, or a method using gene-introducing lipids (Lipofectamine, Lipofectin; Gibco-BRL). Following the introduction, the cells are cultured in a conventional medium containing a selection marker, whereby transformants containing the expression vector can be selected.

The peptide of the present invention can be produced by culturing the obtained transformed cells under appropriate conditions. The resulting peptide may be further isolated and purified by standard biochemical purification procedures. Purification procedures include salting out, ion exchange chromatography, adsorption chromatography, affinity chromatography, gel filtration chromatography, etc. A peptide of the present invention, which has been expressed as a fusion protein with thioredoxin, His-tag, GST, etc, can also be isolated and purified by purification methods which utilize properties of the fusion proteins and the tags.

A polynucleotide encoding a peptide of the present invention may be in the form of either DNA or RNA. These polynucleotides of the present invention can be easily produced, based on the amino acid sequence information of a peptide of the present invention and the sequence information of DNA encoding the amino acid sequence. For example, the polynucleotides can be produced by conventional DNA synthesis and amplification by PCR.

A polynucleotides encoding the peptide of the present invention includes polynucleotides encoding the above-described epitopepeptide.

A nucleic acid comprising a polynucleotide encoding a peptide of the present invention may be in the form of single or double strands. When a polynucleotide of the present invention is a double strand, an expression vector for expressing the peptide of the present invention can be constructed by inserting the above-described polynucleotide into an expression vector.

Expression vectors, host cells, and method of transforming host cells, etc., which are used for this purpose are similar to those described above.

3) An Agent for Inducing CTL Comprising a Peptide of the Present Invention as an active Ingredient A peptide of the present invention can serve as an agent for inducing CTL, which has a CTL inducing activity. An induced CTL is capable of exerting anti-tumor effects via cytotoxic effects and production of lymphokines. Therefore, a peptide of the present invention can be an active ingredient of a pharmaceutical composition for the treatment or prevention of tumors. When a patient with a tumor is administered with an agent for inducing CTL comprising a peptide of the present invention as an active ingredient, the peptide of the present invention is presented to an HLA-A2 antigen of antigen presenting cells, and a CTL specific for a combined complex of the HLA-A2 antigen and the presented peptide can proliferate to kill tumor cells, and consequently, the tumor of the patient can be treated or prevented.

An agent for inducing CTL comprising a peptide of the present invention as an active ingredient can be used for patients with tumors who are positive for the PBF protein shown in SEQ ID NO:2 and an HLA-A2 antigen. For example, the agent for inducing CTL can be used, for example, for the prevention or treatment of all kinds of sarcomas including osteosarcoma, or cancers (tumors) including renal cancer.

An agent for inducing CTL comprising a peptide of the present invention as an active ingredient may comprise a single CTL epitope (a peptide of the present invention) as an active ingredient, or a polyepitope peptide linked to other peptides (CTL epitope and helper epitope) as an active ingredient.

Recently, polyepitope peptides, in which a plurality of CTL epitopes (antigenic peptides) are coupled, have been shown to display CTL inducing activities efficiently in vivo. For example, Journal of Immunology, 1998, 161: 3186-3194, which is incorporated herein by reference, describes that about 30-mer polyepitope peptides, in which CTL epitopes restricted to HLA-A2, -A3, -A11, B53 and derived from a cancer antigen protein PSA (antigenic peptides) were coupled, induced CTLs specific for the respective CTL epitopes in vivo. It is also demonstrated that CTLs are efficiently induced by polyepitope peptides, in which a CTL epitope and a helper epitope were coupled. When an agent for inducing CTL is administered in the form of polyepitope peptides, the polyepitope peptide is incorporated into an antigen presenting cell; intracellular degradation of the polyepitope peptide generates respective antigen peptides, which bind to HLA antigen to form complexes; the complexes are presented on the surface of antigen-presenting cells in high density; CTLs specific for the complexes efficiently proliferate in the body; and kill the tumor cells. In this way, treatment or prevention of tumors is achieved An agent for inducing CTL comprising a peptide of the present invention as an active ingredient can be administered in admixture with, or in combination with, pharmaceutically acceptable carriers such as appropriate adjuvants so that cellular immunity is effectively established.

Examples of adjuvants which are applicable include those described in the literature, Clin. Microbiol. Rev., 7:277-289, 1994, which is incorporated herein by reference. For example, the adjuvants include microorganisms-derived components or their derivatives, cytokines, plant-derived components or their derivatives, marine organism-derived components or their derivatives, mineral gels like aluminum hydroxide, lysolecithin, surfactants like Pluronic polyols, polyanions, peptides, oily emulsions (emulsion formulations), etc. Also contemplated are liposome formulations, particulate formulations which are attached to beads having a diameter of several micrometers, formulation having lipids attached thereto, microsphere formulations, microcapsule formulations, etc.

A Method of administration includes intradermal, subcutaneous, intramuscular, intravenous administration, etc. The dosage of a peptide of the present invention in the formulation can be adequately adjusted, depending on the disease to be treated, the age and weight of the patient, etc. Usually, the dosage of a peptide of the present invention in the formulation is 0.0001 to 1000 mg, preferably 0.001 to 1000 mg, more preferably 0.1 to 10 mg, which is preferably administered once every several days or months.

4) An Agent for Inducing CTL Comprising Nucleic Acids of the Present Invention as an Active Ingredient A cell expressing a nucleic acid of the present invention has a characteristic of being recognized by CTLs. Accordingly, a nucleic acid of the present invention is an inducer of CTLs. The induced CTL is capable of exerting anti-tumor effects through cytotoxic effects or production of lymphokines. Therefore, a nucleic acid of the present invention can be an active ingredient of a medicine for the treatment or prevention of tumors. An agent for inducing CTL comprising a nucleic acid of the present invention as an active ingredient can treat or prevent tumors, for example, by administering a nucleic acid of the present invention to patients with tumors and allowing it to be expressed.

For example, when a nucleic acid of the present invention which has been incorporated into an expression vector is administered to tumor patients by procedures described below, the tumor antigen peptide is highly expressed in antigen presenting cells. The resulting tumor-antigen peptide binds with an HLA-A2 antigen to form a complex, which is presented in high densities on the surface of antigen presenting cells; CTLs specific for the complex efficiently proliferate in the body, and kill tumor cells. In this way, treatment or prevention of tumors is achieved.

An agent for inducing CTL comprising a nucleic acid of the present invention as an active ingredient can be used for tumor patients who are positive for the PBF gene shown in SEQ ID NO:1; the PBF protein, which is an expression product of said gene; and an HLA-A2 antigen. For example, an agent for inducing CTL can be used for the prevention or treatment of all kinds of sarcomas such as osteosarcoma or cancers such as renal cancer.

Administrating a nucleic acid of the present invention and introducing it into cells may be achieved by any of methods using viral vectors and other methods (NIKKEI SAIENNSU [Nikkei Science], 1994, April Issue, pp. 20-45; GEKKAN YAKUZI [The Pharmaceuticals Monthly], 36 (1), 23-48 (1994); ZIKKEN IGAKU ZOUKAN [Experimental Medicine, Supplement], 12 (15), (1994), and references cited therein, which are incorporated herein by reference).

Examples of a method using viral vectors include a method in which a DNA of the present invention is incorporated into a DNA or RNA virus such as retrovirus, adenovirus, adeno-associate virus, herpes virus, vaccinia virus, poxvirus, poliovirus, and Sindbis virus. Among these methods, methods using retrovirus, adenovirus, adeno-associate virus, vaccinia virus, etc., are particularly preferable.

Examples of other methods include a method in which an expression plasmid is directly injected into muscles (DNA vaccination), a method using liposomes, Lipofectine, a microinjection method, a method using calcium phosphate or an electroporation method, and others. Particularly, DNA vaccination and method using liposome are preferable.

Methods which allow a nucleic acid of the present invention to work actually as a pharmaceutical agent include in vivo method in which the nucleic acid is introduced directly into the body, and ex vivo method in which a certain type of cells are collected from a human individual and the nucleic acid is introduced in vitro into the cells, which are then returned back to the body of the individual (NIKKEI SAIENNSU [Nikkei Science], 1994, April Issue, pp. 20-45; GEKKAN YAKUZI [The Pharmaceuticals Monthly], 36 (1), 23-48 (1994); ZIKKEN IGAKU ZOUKAN [Experimental Medicine, Supplement], 12 (15), (1994), and references cited therein, which are incorporated herein by reference). An in vivo method is more preferred.

In case of administration by in vivo method, a nucleic acid of the present invention is administrated via appropriate routes of administration in accordance with the disease to be treated, symptoms, etc. For example, a nucleic acid of the present invention can be administrated intravenously, intraarterially, subcutaneously, intradermally, intramuscularly, etc. In case of administration by in vivo method, a nucleic acid of the present invention may be administered in various formulations such as liquid formulations, and typically, is formulated as an injectable formulation comprising the nucleic acid of the present invention that is an active ingredient, to which pharmaceutically acceptable carriers may be added, if needed. In addition, in case of liposomes or membrane-fused liposomes (e.g., Sendai virus (HVJ)-liposomes) comprising a nucleic acid of the present invention, they may be in the form of liposomal formulations such as suspension, frozen formulation, and centrifugally-concentrated frozen formulations.

The amount of a nucleic acid of the present invention in formulations can be adequately adjusted, depending on the disease to be treated, the age and weight of the patient, etc. It is usually preferable that as the amount of polynucleotide in the nucleic acid, 0.0001 to 100 mg, preferably 0.001 to 10 mg, of a nucleic acid of the present invention is administered once every several days or months.

Recently, a polynucleotide encoding a polyepitope peptide, in which a plurality of CTL epitopes (antigenic peptides) are coupled, or a polynucleotide encoding a polyepitope peptide, in which one or more CTL epitopes and a helper epitope are coupled, have been shown to have CTL inducing activities efficiently in vivo. For example, Journal of Immunology, 1999, 162: 3915-3925, which is incorporated herein by reference, describes that a DNA (minigene) encoding polyepitope peptides, in which HBV-derived six antigenic peptides restricted to HLA-A2, three antigenic peptides restricted to HLA-A11, and a helper epitope were coupled, effectively induced CTLs directed to the respective CTL epitopes in vivo.

Therefore, a polynucleotide prepared by coupling one or more polynucleotides encoding a peptide of the present invention and optionally an additional polynucleotide encoding other peptides can be used as an active ingredient of agents for inducing CTL after incorporating the resulting polynucleotide into an appropriate expression vector. The methods and modes of administration which are similar to those described above are also applicable to this type of agent for inducing CTL.

5) Antigen Presenting Cells of the Present Invention

A peptide and a nucleic acid of the present invention as described above can be used in vitro as described below, in the treatment of tumor patients. For example, an antigen presenting cell can be generated by contacting in vitro either peptide or nucleic acid of the present invention with a cell having antigen-presenting capability. For example, the present invention provides an antigen presenting cell presenting a complex of an HLA-A2 antigen and a peptide of the present invention on the surface of the cell and a method of production thereof, wherein the antigen presenting cell is obtained by in vitro contacting isolated cells having antigen-presenting capability derived from a tumor patient with either peptide or nucleic acid of the present invention.

As used herein, "a cell having antigen-presenting capability" is not limited to a particular cell, provided that the cell expresses on the cell surface an HLA-A2 antigen which is capable of presenting a peptide of the present invention. In particular, dendritic cells having high antigen-presenting capability are preferable.

Substances which are added to prepare an antigen presenting cell of the present invention from the above-described cells having antigen-presenting capability may be either peptide or nucleic acid of the present invention.

An antigen presenting cell of the present invention may be obtained by isolating cells having antigen-presenting capability from a tumor patient, pulsing the cells in vitro with a peptide of the present invention, and allowing an antigen presenting cell to present a complex of an HLA-A2 antigen and the peptide (Cancer Immunol. Immunother., 46:82, 1998; J. Immunol., 158, p. 1796, 1997; and Cancer Res., 59, p. 1184, 1999, which are incorporated herein by reference). When dendritic cells are used, an antigen presenting cell of the present invention can be prepared, for example, by isolating lymphocytes from peripheral blood of a tumor patient using a Ficoll method, removing non-adherent cells, culturing adherent cells in the presence of GM-CSF and IL-4 to induce dendritic cells, and culturing and pulsing the dendritic cells with a peptide of the present invention.

In the case where an antigen presenting cell of the present invention is prepared by introducing a nucleic acid of the present invention into the above-described cells having antigen-presenting capability, the nucleic acid may be in the form of DNA or RNA. For example, in the case where the nucleic acid is a DNA, these procedures can be done, for example, with reference to Cancer Res., 56, p. 5672, 1996; and J. Immunol., 161, p. 5607, 1998, which are incorporated herein by reference, and in the case where the nucleic acid is an RNA, these procedures can be done, for example, with reference to J. Exp. Med., 184, p. 465, 1996, which is incorporated herein by reference.

An antigen presenting cell as described above can be served as an active ingredient of an agent for inducing CTL. An agent for inducing CTL comprising the antigen presenting cell as an active ingredient preferably comprises saline, phosphate buffered saline (PBS), medium, or the like, in order to stably maintain the antigen presenting cells. A Method of administration includes intravenous, subcutaneous, intradermal administration. An agent for inducing CTL comprising the antigen presenting cell as an active ingredient can be returned back into the body of the patient, and thus a specific CTL can be efficiently induced in the body of the patient who is positive for a PBF of the present invention, and, as a result, the tumor can be treated.

6) CTLs of the Present Invention

A peptide and a nucleic acid of the present invention can be used in vitro in the treatment of tumor patients, as follows. In other words, either peptide or nucleic acid of the present invention and peripheral blood lymphocytes can be contacted in vitro to induce CTLs. For example, the present invention provides a CTL induced by contacting in vitro peripheral blood lymphocytes derived form a tumor patient with any of the peptide or nucleic acid of the present invention, and a method of inducing the CTL.

In the case of melanoma, for example, therapeutic effects have been observed in adoptive immunotherapies, in which tumor-infiltrating T-cells from a patient are cultured in vitro in large amounts, followed by returning them back to the patient (J. Natl. Cancer. Inst., 86:1159, 1994, which is incorporated herein by reference). Also, in the case of mouse melanoma, the suppression of metastasis has been found after spleen cells are stimulated in vitro with a tumor antigen peptide TRP-2 to proliferate CTLs specific for the tumor antigen peptide, and administering the CTL to melanoma-implanted mice (J. Exp. Med., 185:453, 1997). This is based on results of in vitro proliferation of CTLs which specifically recognize a complex of an HLA antigen of antigen presenting cells and the tumor antigen peptide. Therefore, therapies, in which peripheral blood lymphocytes from a patient are stimulated with a peptide or nucleic acid of the present invention to proliferate tumor-specific CTLs, and then, the CTLs are returned back to the patient, is believed to be useful.

The CTLs can be used as an active ingredient of an agent for treating or preventing tumors. The agent for treating or preventing tumors preferably comprises saline, phosphate buffered saline (PBS), medium, and the like, in order to stably maintain the CTL. A Method of administration includes intravenous, subcutaneous, intradermal administration. By returning the agent for treating or preventing a tumor comprising the CTLs as an active ingredient back into the body of the patient who is positive for a PBF of the present invention, the cytotoxic action of the CTLs is enhanced in the body of patient so that the tumor cells are killed, and consequently, the tumor can be treated.

7) An Antibody Against Peptides of the Present Invention

The present invention provides an antibody which specifically binds to a peptide of the present invention. An antibody of the present invention is not limited to particular forms, and may be a polyclonal or monoclonal antibody which is raised against a peptide of the present invention.

An antibody of the present invention is not limited to a particular antibody, as long as the antibody specifically binds to a peptide of the present invention, as described above. Examples of an antibody of the present invention include antibodies which specifically bind to a tumor antigen peptide consisting of the amino acid sequence of SEQ ID NO:4.

A method of preparing these antibodies are already well-known, and the antibody of the present invention also can be prepared in accordance with these conventional procedures (Current protocols in Molecular Biology, Edited by Ausubel et al. (1987), Published by John Wiley and Sons, Sections 11.12 to 11.13; Antibodies: A Laboratory Manual, Edited by Lane, H, D. et. al., Published by Cold Spring Harber Laboratory Press, New York, 1989, which are incorporated herein by reference).

For example, a peptide of the present invention (e.g., a tumor antigen peptide consisting of the amino acid sequence of SEQ ID NO:4) is used as an immunogen, and a non-human animal such as rabbit is immunized with the peptide of the present invention to obtain an antibody from anti-serum of the immunized animal using a conventional method. In the case of monoclonal antibodies, on the other hand, a monoclonal antibody can be obtained from a hybridoma cell prepared by fusion of a myeloma cell and a spleen cell which is obtained by immunizing a non-human animal such as mouse with a peptide of the present invention (e.g., a tumor antigen peptide consisting of the amino acid sequence of SEQ ID NO:4) (Current protocols in Molecular Biology, Edited by Ausubel et al., (1987), Published by John Wiley and Sons, Sections 11.4 to 11.11, which is incorporated herein by reference).

An antibody against a peptide of the present invention can be prepared by enhancing immunological reactions using a variety of adjuvants, depending on hosts. Such adjuvants include Freund's adjuvant, mineral gels such as aluminum hydroxide, lysolecithin, Pluronic polyols, polyanions, peptides, oily emulsions, keyhole limpet hemocyanin, surfactants such as dinitrophenol, and human adjuvants, such as BCG (Calmette-Guerin *bacillus*) and *Corynebacterium parvum*.

As mentioned above, an antibody recognizing a peptide of the present invention and further, an antibody neutralizing its activity can be prepared by adequately immunizing animals with a peptide of the present invention using a conventional procedures. The antibody may be used for affinity chromatography, immunological diagnosis, and the others. An immunological diagnosis can be adequately selected from immunoblot, radioimmunoassay (RIA), enzyme-linked immunoassay (ELISA), fluorescent or luminescent measurement methods. These immunological diagnoses are effective for the diagnosis of cancers expressing the PBF gene of the present invention such as sarcomas and renal cancers.

8) Tumor Markers (i) A Tumor Marker Related to Polynucleotides of the Present Invention A tumor marker of the present invention is characterized in that it consists of the above-described polynucleotide of the present invention (a polynucleotide encoding a protein comprising the amino acid sequence identical or a substantially identical to the amino acid sequence of SEQ ID NO:4) and/or a polynucleotide complementary thereto.

For example, a tumor marker of the present invention can include one which consists of a polynucleotide consisting of the nucleic acid sequence of SEQ ID NO:3 and/or a polynucleotide complementary thereto.

As used herein, a complementary polynucleotide (complementary strand, reverse strand) refers to a polynucleotide which has the relationship of base complementarity, based on base pairing such as A:T and G:C, to the sequence of a polynucleotide consisting of the nucleic acid sequence of SEQ ID NO:3 (which is referred as herein to "a forward strand," for convenience).

A polynucleotide of the forward strand may comprise not only a polynucleotide consisting of the nucleic acid sequence of SEQ ID NO:3 but also a polynucleotide consisting of a nucleic acid sequence which has the relationship of complementarity to the nucleic acid sequence of the above-described complementary strand.

Each of the above-described polynucleotide of the forward strand and the above-described polynucleotide of the complementary strand (reverse strand) may be used as a tumor marker in the form of single or double strands.

For example, a tumor marker of the present invention may be a polynucleotide consisting of the nucleic acid sequence of SEQ ID NO:3, or a polynucleotide consisting of its complementary sequence.

A tumor marker of the present invention can be designed, for example, using a software Primer 3 (HYPERLINK, http://www.genome.wi.mit.edu/cgi-bin/primer/primer3.cgi) or Vector NTI (Infomax), for example, based on the nucleic acid sequence of SEQ ID NO:3. For example, candidate sequence of primer or probe which is obtained by applying the nucleic acid sequence of the above-described gene of the present invention to a software Primer 3 or Vector NTI, or sequences comprising at least a part of the candidate sequence can be used as a primer or a probe.

The length of a tumor marker of the present invention can be adequately selected, depending on particular applications of the marker.

Detection (diagnosis) of a tumor, in one embodiment of the present invention, is performed by evaluating the presence or absence of or the level (amount) of expression of a gene of a peptide of the present invention in a biological tissue of a subject, particularly, in a tissue to be tested which is suspected of being affected with a tumor (sarcoma or renal cancer). In this case, the above-described tumor marker of the present invention can be used as a primer for specifically recognizing and amplifying an RNA which is generated by the expression of a gene of a peptide of the present invention or a polynucleotide derived therefrom, or as a probe for specifically detecting the RNA or a polynucleotide derived therefrom.

In the case of using a tumor marker of the present invention as a primer for the detection of a tumor, the primer can include a primer which preferably has a base length of 15 to 30 bp. In the case of using a tumor marker of the present invention as a detection probe, the probe can include a probe which preferably has a bases length of 15 to 27 bp.

The tumor markers of the present invention can be used as a primer or a probe for a method which is known to specifically detect a particular gene, including Northern blotting, RT-PCR, in situ hybridization methods, and others, in accordance with conventional procedures.

A tumor marker of the present invention is useful for the diagnosis and detection of a tumor (diagnosis of the presence or absence of and the degree of the disease). For example, the diagnosis of tumor using a tumor marker of the present invention can be made by determining the difference in the level of gene expression of a gene of a peptide of the present invention between a biological tissue of a subject (tissue suspected of being affected with a tumor) and its corresponding tissue of a healthy individual. In this case, the difference in the level of gene expression includes not only the presence or absence of the gene expression but also two or more times higher differences, preferably three or more times higher differences in the amount of gene expression between the subject and the healthy individual in the case where the gene expression is detected in both of the tissues of the subject and the healthy individual. For example, since the expression of a gene of a peptide of the present invention is induced in a tumor, a subject whose tissue displays its expression and an amount of said gene expression is two or more times higher, preferably three or more times higher than that in the corresponding tissue of a healthy individual is suspected to be affected by tumor.

(ii) A Tumor Marker Related to Antibodies of the Present Invention

The present invention provides, as a tumor marker, an antibody capable of specifically recognizing a peptide of the present invention, which is hereinafter sometimes referred to as an antibody of the present invention. More specifically, the present invention provides a tumor marker consisting of an antibody which specifically recognizes a peptide of the present invention consisting of the amino acid sequence of SEQ ID NO:4.

In various sarcomas and renal cancers, it has been found that PBF genes are specifically and highly expressed. Therefore, detection of the presence or absence of expression products (peptides) of these genes or the degree of their expression enables people to specifically detect the presence or absence or the degree of the above-described tumors such as sarcomas and renal cancers so that the disease can be diagnosed.

Therefore, the above-described antibody is useful as a tool (tumor marker) for diagnosing whether or not the subject is affected with a tumor, or what degree of the disease the subject has by detecting the presence or absence or the degree of expression of the above-described peptides in a subject.

The antibody of the present invention is not limited to particular forms, and may be a polyclonal or monoclonal antibody raised against a peptide of the present invention (specifically, a peptide consisting of the amino acid sequence of SEQ ID NO:4). A Method of producing the antibody is already well-known, and an antibody of the present invention also can be produced in accordance with these conventional procedures (Current protocols in Molecular Biology, Sections 11.12 to 11.13 (2000), which is incorporated herein by reference). For example, when the antibody of the present invention is a polyclonal antibody, a polyclonal antibody can be obtained by purifying a peptide of the present invention which is expressed in *Escherichia coli* or the like using conventional procedures or synthesizing a peptide of the present invention using conventional procedures; immunizing non-human animal such as rabbit with the peptide; and obtaining a polyclonal antibody from antiserum of the immunized animal using conventional procedures. When the antibody of the present invention is a monoclonal antibody, on the other hand, a monoclonal antibody can be obtained from a hybridoma prepared by immunizing non-human animal such as a mouse with a peptide of the present invention, which is expressed in *Escherichia coli* or the like followed by purification using conventional method; and carrying out cell fusion of spleen cells obtained from the immunized animal and myeloma cells (Current protocols in Molecular Biology, Edited by Ausubel et al., (1987) Published by John Wiley and Sons, Sections 11.4 to 11.11, which is incorporated herein by reference).

A peptide of the present invention which is used as an immunogen for the preparation of an antibody (in particular, a peptide consisting of the amino acid sequence of SEQ ID NO:4) can be obtained by procedures as follows: DNA cloning; construction of plasmids; transfection into a host cell; culturing the transformants; and collection of the peptide from the culture, based on the sequence information of the gene provided by the present invention (SEQ ID NO:3). These procedures can be performed, for example, in accordance with methods already known to those skilled in the art or methods described in the literature: Molecular Cloning, T. Maniatis et al., CSH Laboratory (1983); DNA Cloning, D M.

Glover, IRL PRESS (1985), which are incorporated herein by reference. A peptide of the present invention can be produced by conventional chemical synthesis (peptide synthesis) according to the information of the amino acid sequence provided by the present invention (SEQ ID NO:4). See sections 1) and 2) described previously, for detail.

(iii) A Tumor Marker Related to Peptides of the Present Invention

The present invention provides, as a tumor maker, a peptide capable of specifically recognizing an antibody against a peptide of the present invention. For example, the present invention provides a tumor marker consisting of a peptide of the present invention consisting of the amino acid sequence of SEQ ID NO:4.

Diagnosis of a tumor can be made by using a peptide (polypeptide) of the present invention as a diagnostic agent and detecting the presence of such an antibody in samples taken from a patient suspected of being affected with a tumor, such as blood, tissues suspected of being affected with a tumor, and others. A Method for producing a peptide of the present invention is as described above in section 1).

For example, an antibody against PBF can be detected by collecting blood of a patient or taking specimens of a tissue suspected of being affected with a tumor, for example, by biopsy; preparing peptides therefrom using conventional procedures; and using a peptide of the present invention as a probe in accordance with conventional procedures, for a known method of detection such as Western blotting, ELISA, and other methods.

For diagnosis of a tumor, the difference in the amount of antibody against a peptide of the present invention between specimens of a tissue of a subject and the corresponding normal tissue may be determined. In this case, the difference in the amount of peptide includes the case where the protein is either presence or absence, and the amount of the protein differs at least by 2-fold, preferably 3-fold.

For example, since the expression of a gene of the peptide of the present invention is induced in a tumor such as sarcoma and renal cancer, the subject is suspected of being affected with a tumor disease, if an antibody against an expression product of the gene (a peptide of the present invention) is present in tissue specimens of a subject, and the antibody against the peptide of the present invention is determined to be present in tissue specimens of the subject in two or more times higher amount, preferably three or more times higher amount than that in specimens of a normal tissue.

(iv) A Tumor Marker Related to HLA Tetramers

The present invention also provides an HLA tetramer comprising a peptide of the present invention and an HLA-A2 antigen, and a tumor marker consisting of the HLA tetramer.

As used herein, an HLA tetramer refers to a tetramer formed by biotinylating a complex (HLA monomer) in which the a strand of an HLA antigen and β-2 microglobulin are associated with a peptide (antigenic peptide), and binding the complex to avidin (Science, 279:2103-2106 (1998); Science, 274:94-96 (1996), which are incorporated herein by reference). At present, a variety of HLA tetramers comprising different antigenic peptides are commercially available (e.g., from Medical & Biological Laboratories Co., Ltd.), and HLA tetramers comprising a peptide of the present invention and an HLA-A2 antigens can be easily produced.

A example includes an HLA tetramer comprising a tumor antigen peptide consisting of the amino acid sequence of SEQ ID NO:4 and an HLA-A2 antigen.

The HLA tetramer is preferably fluorescence-labeled so that CTLs attached thereto can be easily selected or detected by known means of detection such as flow cytometry, fluorescence microscope, etc. For example, an HLA tetramer is labeled with phycoerythrin (PE), fluorescein isothiocyanate (FITC), Peridinin-chlorophyll -protein (PerCP), or the like.

A Method of preparing HLA tetramers is well-known by the literature: Science, 279:2103-2106 (1998); Science, 274: 94-96 (1996), which are incorporated herein by reference. The method is briefly explained as follows.

First, a HLA-A2 α-chain expression vector and aβ-2 microglobulin expression vector are introduced into *Escherichia coli* or mammalian cells capable of protein expression to express the proteins. *Escherichia coli* such as BL21 is preferably used. The resulting monomeric HLA-A2 complex and a peptide of the present invention are mixed to form a soluble HLA-peptide complex. Then, the HLA-peptide complex is biotinylated with the BirA enzyme at the C-terminal sequence of HLA-A24 α-chain. The biotinylated HLA-peptide complex and a fluorescently-labeled avidin are mixed at a molar ratio of 4:1 so that an HLA tetramer can be prepared. In each of the steps described above, the protein is preferably purified by gel filtration etc.

(v) A Method of Tumor Detection (Method of Diagnosis)

The present invention provides a method of the detection (diagnosis) of a tumor using the above-described tumor marker of the present invention.

For example, the detection (diagnosis) method according to the present invention is a method in which blood of a patient is collected, or a part of a tissue to be tested which is suspected of being affected with a tumor is removed, for example, by biopsy; the amount of CTLs which recognize a complex contained therein of a PBF-derived tumor antigen peptide and an HLA antigen is detected and measured; and thereby, the presence or absence or the degree of a tumor disease such as sarcoma, renal cancer, etc., is diagnosed. For example, when the therapeutic agent is administered to patients with tumor to ameliorate the tumor, the detection (diagnosis) method according to the present invention can be also used to detect (diagnose) the presence or absence or the degree of the amelioration of the disease. In addition, the detection (diagnosis) method according to the present invention can be used, for example, for selecting tumor patients to whom a pharmaceutical composition comprising a peptide or nucleic acid of the present invention as an active ingredient is applicable and further, for determining therapeutic effects of the pharmaceutical composition.

The detection (diagnosis) method according to the present invention comprises the following steps:

(a) a step of contacting a biological sample of a subject with a tumor marker of the present invention;
(b) a step of measuring as an indicator of the tumor marker, the amount of CTLs which recognize a complex of a PBF-derived tumor antigen peptide and an HLA antigen contained in the biological sample; and
(c) a step of judging, on the basis of the results of (b), whether the subject is suffering from a tumor.

Biological samples which are used herein can include samples or specimens which are prepared from biological tissues of patients (e.g., a tissue suspected of being affected with a tumor and its surrounding tissues, blood, etc.). For example, biological samples may include RNA containing samples prepared from said tissues or samples comprising polynucleotides obtained by further preparing said samples, or samples comprising peptides or antibodies prepared from said tissues, or samples comprising peripheral blood lymphocytes prepared from said tissues.

The diagnostic methods according to the present invention are carried out in particular as described below, depending on the type of biological samples used as a measurement target.

((v)-1) In Case of Using RNAs as Biological Samples to be Measured

When an RNA is used as a measurement target, a tumor can be detected by a method which comprises in particular, the following steps (a)-(c):
(a) a step of binding an RNA prepared from a biological sample of a subject or a complementary polynucleotide transcribed therefrom to the above-described tumor marker of the present invention (a polynucleotide of the present invention and/or a polynucleotide complementary thereto);
(b) a step of measuring the RNA derived from the biological sample or the complementary polynucleotide transcribed therefrom which is bound to the tumor marker, using the tumor marker as an indicator; and
(c) a step of judging, on the basis of results of the measurement of (b), whether the subject is suffering from a tumor.

When an RNA is used as a measurement target, the detection (diagnosis) method according to the present invention is carried out by detecting and measuring the level of expression of the gene of the present invention in the sample-derived RNAs. For example, the detection (diagnosis) method according to the present invention can be carried out by known methods such as Northern blotting, RT-PCR, DNA chip analysis, in situ hybridization analysis, and others, using a tumor marker of the present invention consisting of the above-described polynucleotide (a polynucleotide of the present invention and or a polynucleotide complementary thereto) as a primer or probe.

In the case of employing Northern blotting, the presence or absence or the level of expression of a gene of the present invention in the sample-derived RNAs can be detected and measured by using the above-described tumor marker of the present invention as a probe. For example, the method is carried out as follows: a tumor marker of the present invention (a complementary strand) is labeled with a radioisotope (e.g., $^{32}P$, $^{33}P$, and others; RI), fluorescent substance, or the like; the labeled tumor-marker is hybridized to RNAs derived from a biological sample of a subject which have been transferred onto a nylon membrane etc using a conventional procedure; and then the double strand formed by the tumor marker (DNA) and the RNA is detected and measured by detecting and measuring the signal from the label of the labeled tumor-marker (RI or fluorescent substance) with a radiation detector (BAS-1800II, FUJIFILM Corporation) or fluorescence detector. Alternatively, the method may be carried out as follows: AlkPhos Direct Labelling and Detection System (Amersham Pharmacia Biotech) is used to label a tumor marker (a probe DNA) following its protocol, which is then hybridized to the RNAs derived from a biological sample of a patient; and the signal from the label of the labeled tumor-marker is detected and measured with a Multi Bio Imager STORM 860 (Amersham Pharmacia Biotech).

In case of employing RT-PCR, the presence or absence, or the level of expression of a gene of the present invention in the sample-derived RNAs can be detected and measured by using the above-described tumor marker of the present invention as a primer. For example, the method is carried out as follows: cDNA is prepared from the RNAs derived from a biological sample of a subject using a conventional procedure; after hybridizing the cDNA with a pair of primers prepared from a tumor marker of the present invention (a forward primer binding to the above-described cDNA (minus strand) and a reverse primer binding to the positive strand), a PCR is conducted using a conventional procedure so that the gene of the present invention can be amplified using the cDNA as a template; and then, the resulting amplified double-stranded DNA is detected. The detection of the amplified double-strand DNA can be achieved by, for example, a method in which the above-described PCR is performed with a primer which has been labeled in advance with an RI or fluorescent substance and the resulting labeled double-stranded DNA is detected; or a method in which the resulting double-stranded DNA is transferred onto a nylon membrane, etc., using a conventional procedure and hybridized with a labeled tumor-marker which is used as a probe, thereby detecting the double-stranded DNA. The resulting labeled double-stranded DNA product can be measured by an Agilent 2100 Bioanalyzer (Yokogawa Analytical System), for example. In addition, RT-PCR can be carried out as follows: RT-PCR reaction mixture is prepared using SYBR Green RT-PCR Reagents (Applied Biosystems) following the protocol; the reaction is carried out using an ABI PRISM 7700 Sequence Detection System (Applied Biosystems); and the reaction product is detected.

In the case of employing DNA chip analysis, for example, the method is carried out as follows: a DNA chip onto which the above-described tumor markers of the present invention are attached as a DNA probe (single or double strand) is prepared; the DNA chip is hybridized to cRNAs which are prepared using conventional procedures from RNAs derived from biological samples of patients; and the resulting double strand formed by the DNA and the cRNA binds to a labeled probe prepared from the tumor marker of the present invention; and the double strand bound to the labeled probe is detected.

((v)-2) In the Case of Using a Peptide as Biological Samples to be Measured

When a peptide is used as a measurement target, the method of the detection (diagnosis) of a tumor according to the present invention is carried out by detecting a peptide of the present invention and measuring its amount. For example, the method according to the present invention can be carried out by a method comprising the following steps:
(a) a step of binding peptides prepared from a biological sample of a subject to a tumor marker of the present invention which is directed to an antibody (PBF-recognizing antibody);
(b) a step of measuring, with the tumor marker as an indicator, the peptide derived from the biological sample which is bound to the tumor marker; and
(c) a step of judging, on the basis of results of the measurement of (b), whether the subject is suffering from a tumor.

For example, the method is carried out by detecting and quantifying a peptide of the present invention using an antibody (an antibody which recognizes a peptide of the present invention) as a tumor marker of the present invention according to known methods such as Western blotting.

Western blotting can be carried out as follows: a tumor marker of the present invention are used as a primary antibody, and subsequently, a labeled antibody which is labeled with a radioisotope such as $^{125}I$, fluorescent substance, enzyme (e.g., horseradish peroxidase (HRP)), etc., is used as a secondary antibody, which is an antibody binding to the primary antibody; and the obtained signal from the radioisotope, fluorescent substance, etc., of the labeled compound is detected and measured, for example, with a radiation detector (e.g., BAS-1800II, FUJIFILM Corporation) or fluorescence detector. Alternatively, Western blotting can be carried out as follows: after a tumor marker of the present invention is used as a primary antibody, ECL Plus Western Blotting Detection System (Amersham Pharmacia Biotech) is used for the detection according to its protocol; and the signal is measured with a Multi Bio Imager STORM 860 (Amersham Pharmacia Biotech).

((v)-3) In the Case of Using an Antibody as Biological Samples to be Measured

When an antibody which is present in a biological sample is used as a measurement target, the method of detection (diagnosis) of a tumor according to the present invention is carried out by detecting an antibody against a peptide of the present invention in a biological sample and measuring its amount. For example, the method according to the present invention can be carried out by using a tumor marker of the present invention which is related to a peptide and performing procedures similar to ((v)-2) as described above.

((v)-4) In Case of Using a Tumor Antigen-specific CTL as Biological Samples to be Measured When tumor antigen-specific CTLs present in peripheral blood lymphocytes are used as a measurement target, the method of detection (diagnosis) of a tumor according to the present invention is carried out by detecting a CTL specific for a peptide of the present invention in a biological sample and measuring its amount. For example, the method according to the present invention can be carried out by preparing a tetramer (HLA tetramer) of a complex which is formed by a fluorescently labeled HLA antigen and a peptide of the present invention in accordance with the method as described in the literature (Science, 274:94, 1996, which is incorporated herein by reference) and using the tetramer to quantify by a flow cytometry CTLs which are specific for the antigen peptide in peripheral blood lymphocytes from a patient who is suspected of being affected with a tumor.

((v)-5) Diagnosis of a Tumor

Diagnosis of a tumor can be carried out, for example, by measuring the level of gene expression of a peptide of the present invention, the amount of a peptide of the present invention which is an expression product of the gene, the amount of an antibody against a peptide of the present invention, or the amount of CTLs specific for a peptide of the present invention in subject's blood and tissue to be tested which is suspected of being affected with a tumor. Optionally, diagnosis may be carried out by comparing the level of expression of said genes or said peptides with that in the corresponding normal tissue, and determining the difference between both tissue of the subject and the corresponding normal tissue.

Comparison of the amount (level) of genes, peptides, antibodies, or CTLs between a tissue to be tested of a subject and the corresponding normal tissue can be carried out by conducting measurements in parallel of biological samples of a subject and a normal individual. When measurements are not conducted in parallel, the comparison can be carried out using a mean value or statistical intermediate value of the results regarding levels of gene expression of a peptide of the present invention, amounts of a peptide of the present invention, amounts of an antibody against a peptide of the present invention, or amounts of CTLs specific for a peptide of the present invention as a normal value, which are obtained by conducting the measurement of a plural of specimens of a normal tissue (at least two, preferably three or more, and more preferably five or more specimens) under uniform conditions Whether or not a subject is suffering from a tumor can be determined, for example, depending on whether or not levels of gene expression of a peptide of the present invention; amounts of a peptide of the present invention; amounts of an antibody against a peptide of the present invention; or amounts of CTLs specific for a peptide of the present invention are two or more times higher, preferably three or more times higher in subject's tissue compared to those in a normal individual's tissue.

The present invention is further illustrated by the following examples, but is not limited by these examples in any respect.

EXAMPLE 1

Synthesis of Peptides and Measurement of their Binding Affinity to HLA-A 0201

A peptide shown in SEQ ID NO:4 was synthesized by the Fmoc method. Binding affinity of the peptide to HLA-A0201 was measured by an HLA class I stabilization assay (J Immunol, 2004, 173:1436, which is incorporated herein by reference). In the assay, a peptide derived from influenza matrix protein (RYLRDQQLLGI, SEQ ID NO:5) was used as a positive control and a murine H-2 Kb binding peptide VSV8 (RGYVYQGL, SEQ ID NO:6) was used as a negative control. The assay was performed in triplicate. The measured binding affinity to HLA-A0201 of the peptides was detected by staining with an FITC-labeled anti-HLA-A2 monoclonal antibody BB7.2 (purchased from ATCC), and measuring the fluorescence signals by a flow cytometry, and determining the percent mean fluorescence Intensity increase (% MFI increase) according to the following equation: % MFI increase=[(MFI with the given peptide−MFI without peptide)/(MFI without peptide)]×100. The % MFI increase±standard deviation (SD) was 44.9±6.8 for the influenza matrix protein derived peptide (SEQ ID NO:5), which was a positive control; 5.6±8.2 for the H-2 Kb binding peptide VSV8 (SEQ ID NO:6), which was negative control; and 74.5±6.6 for the peptide shown in SEQ ID NO:4, indicating that the peptide shown in SEQ ID NO:4 bound to HLA-A0201.

EXAMPLE 2

Frequency Analysis of Antigenic Peptide-specific CTLs

Lymphocytes from five PBF-positive patients with osteosarcoma were subjected to, mixed lymphocyte peptide culture under conditions of limiting dilution (limiting dilution/mixed lymphocyte peptide culture; LD/MLPC) to induce peptide-specific CTLs (Cancer Sci., 2008, 99:368-375, which is incorporated herein by reference). Regarding two patients: Patient Nos. 1, and 2, 50 ml of peripheral blood was collected to isolate peripheral blood mononuclear cells (PBMCs). PBMCs were cultured for 60 minutes at room temperature in AIM-V medium (Invitrogen) containing 1% human serum and supplemented with 50 μg/ml of the peptide shown in SEQ ID NO:4. PBMCs which were pulsed with the peptide were plated at $2 \times 10^5$ cells/200 μl/well on a U-bottomed 96-well microtiter plate and cultured in AIM-V medium containing 10% human serum, 20 U/ml IL-2, and 10 ng/ml IL-7. Seven days after the culture was started, half of the cultured medium in each well was replaced with AIM-V medium containing IL-2, IL-7, and the peptide shown in SEQ ID NO:4 in order to perform the second stimulation. Cells on 14 to 21 days after the culture was started were used for frequency analysis with a tetramer.

Regarding three patients: Patient Nos. 3, 4, and 5, CD8-positive cells were isolated from PBMCs using magnetic anti-CD8 microbeads (Miltenyi Biotec). CD8-positive cells were pulsed for 60 minutes with the peptide shown in SEQ ID NO:4 and inactivated by radiation. $1.0 \times 10^5$ to $2.1 \times 10^5$ CD8- positive cells/well were cultured on a 48-well microtiter plate using AIM-V medium containing 10% human serum, 20 U/ml IL-2, and 10 ng/ml IL-7, together with $2\times10^5$ to $5\times10^5$ cells/well of irradiated, peptide-pulsed CD8-positive cells. After 7 days of the culture, the irradiated peptide-pulsed CD8-positive cells were added as described above, in order to perform the second stimulation. Cells on 13 to 23 days after the culture was started were used for frequency analysis with a tetramer. A PE-labeled HLA-A0201/PBF tetramer (MBL) which was prepared using the peptide shown in SEQ ID NO:4 was used for the analysis.

An FITC-labeled HLA-A0201/HIV tetramer (MBL) which was prepared using an HIV-derived peptide was used as negative control. Some of the lymphocytes which were cultured using the LD/MLPC method were cultured at room temperature for 15 minutes with the PE-labeled HLA-A0201/PBF tetramer or with the FITC-labeled HLA-A0201/HIV tetramer (10 nM each, in 25 μl of PBS), followed by staining. Further, a PE-Cy5-labeled anti-CD8 antibody, eBioscience) was added and incubated for 15 minutes, followed by staining. Then, cells were washed twice with PBS, fixed in 0.5% formalin, and analyzed in a flow cytometer FACScan. Living cells which were stained both with the PE-Cy5-labeled anti-CD8 antibody and with the PE-labeled HLA-A0201/PBF tetramer were considered to be tetramer-positive and peptide-specific CTLs. The frequency of CTLs specific for a peptide shown in SEQ ID, NO:4 was determined using the following equation: Frequency=the number of tetramer-positive wells/(the total number of the wells examined×the number of CD8-positive cells per well at the start of LD/MLPC). Results of CTL frequencies regarding the five patients are shown in Table 2. Of the five patients, three patients: Patient Nos. 4, 3, and 4, had frequencies of $5\times10^{-6}$, $2\times10^{-7}$, and $5\times10^{-7}$, respectively. It was found that CTLs specific for the peptide ,shown in SEQ ID NO:4 were induced.

TABLE 2

| Patient No. | Number of wells tested | Number of tetramer-positive wells | Number of initial cells per well | % CD8 | Frequency |
| --- | --- | --- | --- | --- | --- |
| 1 | 18 | 0 | 200,000 | 25 | $<1\times10^{-6}$ |
| 2 | 46 | 10 | 200,000 | 24 | $5\times10^{-6}$ |
| 3 | 56 | 2 | 210,000 | 99 | $2\times10^{-7}$ |
| 4 | 36 | 3 | 150,000 | 99 | $5\times10^{-7}$ |
| 5 | 103 | 0 | 100,000 | 99 | $<1\times10^{-7}$ |

EXAMPLE 3

Establishing of Antigenic Peptide-specific CTLs

For culturing T cells, B-cell line: NS-EBV-B cells, which were obtained by transforming with EB virus B cells from a healthy individual who was positive for HLA-A0201, and B-cell line: LCL-S2000 cells, which were obtained by transforming with EB virus B cells from a patient with osteosarcoma who was negative for HLA-A0201 (J Orthop Sci., 2003, 8:554-559, which is incorporated herein by reference) were used. T cells from wells of Patient No. 4 which were tetramer-positive found in Example 2 were plated at a single cell/well on a 96-well microplate. To each well were added $2\times10^4$ NS-EBV-B cells which had been irradiated and pulsed with the peptide shown in SEQ ID NO:4 and $8\times10^4$ allogenic PBMCs which had been irradiated, and cultured in 200 μl AIM-V medium containing 10% human serum, 200 U/ml IL-2, and 10 ng/ml IL-7. 14 and 21 days after the culture was started, 100 μl of the medium was replaced with a new medium containing $1\times10^4$ NS-EBV-B cells which had been irradiated and pulsed with the peptide shown in SEQ ID NO:4, $1\times10^4$ LCL-S2000 cells, and $8\times10^4$ allogenic PBMCs which had been irradiated. 35 days after the culture was started, some of the cells in all wells were analyzed with the HLA-A0201/PBF tetramer.

Cells in tetramer-positive wells were collected, and cultured on a U-bottomed 96-well microplate at $2\times10^3$ cells/well in 100 μl AIM-V medium containing 10% human serum, 200 U/ml IL-2, and 7.5 μg/ml phytohemagglutinin P, together with $1\times10^3$ allogenic PBMCs which had been irradiated. Seven days later, 100 μl AIM-V medium containing 10% human serum and IL-2 was added to each well. 14 days later, after all the grown cells were collected, 0.5 to $1\times10^6$ cells were added to each well of 48-well microplate, and cultured in AIM-V medium containing 10% human serum and IL-2. The established cell line was named as CTL5A9. Cytotoxic activities by CTLs were measured by a $^{51}$Cr release assay (J Immunol, 2002, 169:1611-1618, which is incorporated herein by reference).

Osteosarcoma cell lines: U2OS (U2OS, in FIG. 2) and OS2000 (OS2000, in FIG. 2), an erythroleukemia-derived cell line: K562 (K562, in FIGS. 1 and 2), and a lymphoblastic cell line: T2 (T2, in FIG. 1) were used as target cells. U2OS cells are HLA-A0201-positive and PBF-positive, OS2000 cells are HLA-A0201-negative and PBF-positive, and T2 cells are HLA-A0201-positive and PBF-negative. The target cells were labeled with 100 μCi of $^{51}$Cr for one hour. After labeled with $^{51}$Cr, T2 cells were pulsed for one hour with or without 50 μg/ml of the peptide shown in SEQ ID NO:4. U2OS cells were treated for 48 hours with or without 100 U/ml of interferon-γ. FIG. 1 shows the cytotoxic activities of CTL5A9 against T2 cells pulsed with or without the peptide, and against K562 cells. CTL5A9 showed cytotoxic activities only against cells pulsed with the peptide.

Figure 2:
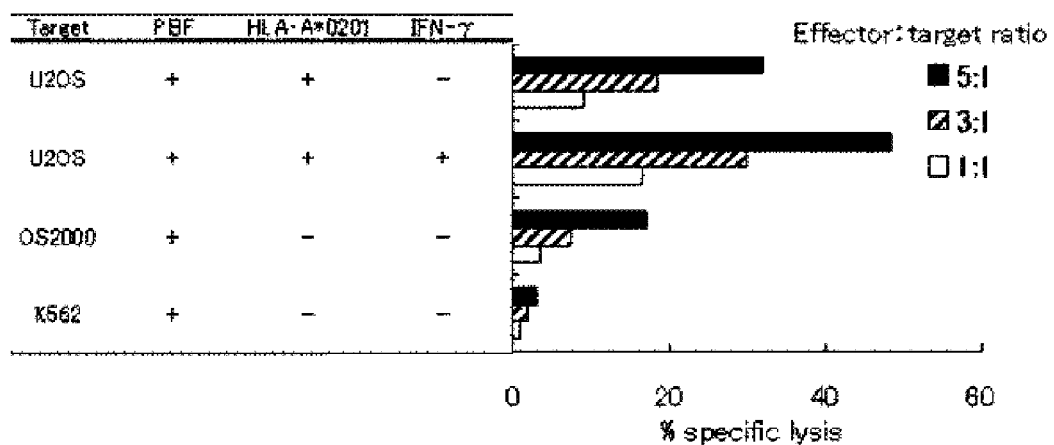
FIG. 2 is a graph showing the cytotoxic effect of CTL5A9 on cancer cell lines. The symbols "+" and "−" indicate the presence or absence of expression of PBF, expression of HLA-A0201 and IFN-γ treatment regarding the respective cell lines. The cytotoxic activity of CTL5A9 for the respective cell lines was determined with varying effector:target ratios.

FIG. 2 shows the cytotoxic activities of CTL5A9 against the osteosarcoma cell lines U2OS and OS2000. CTLA5A9 had cytotoxicity against U2OS cells which are PBF-positive and HLA-A0201-positive and no cytotoxicity against K562 cells which are positive for PBF, but negative for HLA-A0201. When the amount of expression of HLA-A0201 in U2SO cells was increased by the treatment with interferon-γ, U2SO cells were prone to being injured by CTL5A9. These results demonstrated that CTL5A9 recognized a complex of a PBF-derived antigenic peptide produced in cancer cells and HLA-0201, thereby displaying cytotoxic activities.

Industrial Applicability

The present invention provides, for example, use of a tumor antigen protein PBF and its gene as an agent for inducing CTL. The agent for inducing CTL of the present invention can be used to treat patients with sarcoma, renal cancer, etc.

Amino acid sequences shown in SEQ ID NOs:3 to 6 are those of synthetic peptides.

[Sequence Listing]

The invention claimed is:

1. A composition comprising a peptide consisting of the amino acid sequence of SEQ ID NO: 4 as an active ingredient and an effective amount of an adjuvant.

2. A composition comprising a recombinant expression vector comprising a nucleic acid encoding a peptide consisting of the amino acid sequence of SEQ ID NO: 4.

3. The composition according to claim 2, wherein the nucleic acid is a polynucleotide consisting of the nucleic acid sequence of SEQ ID NO:3.

4. A composition comprising a nucleic acid encoding a peptide consisting of the amino acid sequence of SEQ ID NO: 4 and an effective amount of an adjuvant.

5. A method of producing an antigen presenting cell, comprising contacting in vitro:
   (a) a peptide consisting of the amino acid sequence of SEQ ID NO: 4, or
   (b) a nucleic acid comprising a polynucleotide encoding a peptide consisting of the amino acid sequence of SEQ ID NO: 4,
   with a cell having antigen-presenting capability.

6. An antigen presenting cell produced by the method according to claim 5.

7. A method of inducing a CTL, comprising contacting:
   (a) a peptide consisting of the amino acid sequence of SEQ ID NO: 4, or
   (b) a nucleic acid comprising a polynucleotide encoding a peptide consisting of the amino acid sequence of SEQ ID NO: 4,
   with a peripheral blood lymphocyte.

8. A CTL induced by the method according to claim 7.

9. An antibody which specifically binds to a peptide consisting of amino acid sequence of SEQ ID NO: 4.

10. An HLA tetramer which comprises a peptide consisting of the amino acid sequence of SEQ ID NO: 4 and a biotinylated HLA antigen.

11. A method of diagnosing a tumor in patient comprising:
contacting a sample obtained from the patient with the antibody of claim 9,
detecting binding between a peptide in the sample obtained from the patient and the antibody of claim 9; and
determining that the patient is suffering from a tumor upon detecting that the peptide is bound to the antibody.

12. A method of treating cancer, comprising administering to an individual in need thereof a pharmaceutical composition comprising a pharmaceutically acceptable carrier and one of the following:
(a) a peptide consisting of the amino acid sequence of SEQ ID NO: 4,
(b) a nucleic acid consisting of a polynucleotide encoding a peptide consisting of the amino acid sequence of SEQ ID NO: 4, or
(c) an antigen presenting cell produced by the method according to claim 5.

13. A composition comprising a recombinant expression vector comprising a nucleic acid encoding a peptide consisting of the amino acid sequence of SEQ ID NO: 4 and a pharmaceutically acceptable carrier, wherein the composition has activity of inducing CTL when administered to a human or animal model of a human.

14. A peptide consisting of the amino acid sequence of SEQ ID NO; 4 and containing a substitution of an amino acid residue at position 2 or the C-terminus of SEQ ID NO: 4, wherein an amino acid residue at position 2 of SEQ ID NO: 4 is substituted by methionine, valine, isoleucine or glutamine, or an amino acid residue at the C-terminus of SEQ ID NO: 4 is substituted by leucine.

15. A pharmaceutical composition capable of inducing CIL, comprising:
an effective amount for inducing CTL of an isolated or synthesized peptide consisting of the amino acid sequence of SEQ ID NO: 4; and
a pharmaceutical acceptable carrier, wherein the pharmaceutical acceptable carrier is an adjuvant.

16. A method of diagnosing a tumor in a patient, comprising:
contacting a sample obtained from the patient with the HLA tetramer of claim 10;
detecting binding between a CTL in the sample obtained from the patient and the HLA tetramer; and
determining that the patient is suffering from a tumor upon detecting that the CTL is bound to the HLA tetramer,
wherein said HLA tetramer comprises a biotinylated HLA antigen and a peptide consisting of the amino acid sequence of SEQ ID NO:4.

* * * * *

UNITED STATES PATENT AND TRADEMARK OFFICE
CERTIFICATE OF CORRECTION

PATENT NO. : 9,260,499 B2
APPLICATION NO. : 13/125044
DATED : February 16, 2016
INVENTOR(S) : Noriyuki Sato et al.

It is certified that error appears in the above-identified patent and that said Letters Patent is hereby corrected as shown below:

ON THE TITLE PAGE:

At item (73), Assignees, change:

"SAPPORO MEDICAL UNIVERSITY, Sapporo-shi, Hokkaido (JP);
SUMITOMO DAINTPPON PHARMA CO., LTD., Osaka-shi, Osaka (JP)"

to: --SAPPORO MEDICAL UNIVERSITY, Sapporo-shi, Hokkaido (JP);
SUMITOMO DAINIPPON PHARMA CO., LTD., Osaka-shi, Osaka (JP)--.

Signed and Sealed this
Twenty-sixth Day of July, 2016

Michelle K. Lee
*Director of the United States Patent and Trademark Office*

SEQUENCE LISTING

<160> NUMBER OF SEQ ID NOS: 6

<210> SEQ ID NO 1
<211> LENGTH: 1539

```
<212> TYPE: DNA
<213> ORGANISM: Homo sapiens
<220> FEATURE:
<221> NAME/KEY: CDS
<222> LOCATION: (1)..(1539)

<400> SEQUENCE: 1 atg gcg agt gtc ctg tcc cga cgc ctt gga aag cgg tcc ctc ctg gga      48
Met Ala Ser Val Leu Ser Arg Arg Leu Gly Lys Arg Ser Leu Leu Gly
1               5                   10                  15 gcc cgg gtg ttg gga ccc agt gcc tcg gag ggg ccc tcg gct gcc cca      96
Ala Arg Val Leu Gly Pro Ser Ala Ser Glu Gly Pro Ser Ala Ala Pro
            20                  25                  30 ccc tcg gag cca ctg cta gaa ggg gcc gct ccc cag cct ttc acc acc     144
Pro Ser Glu Pro Leu Leu Glu Gly Ala Ala Pro Gln Pro Phe Thr Thr
        35                  40                  45 tct gat gac acc ccc tgc cag gag cag ccc aag gaa gtc ctt aag gct     192
Ser Asp Asp Thr Pro Cys Gln Glu Gln Pro Lys Glu Val Leu Lys Ala
    50                  55                  60 ccc agc acc tcg ggc ctt cag cag gtg gcc ttt cag cct ggg cag aag     240
Pro Ser Thr Ser Gly Leu Gln Gln Val Ala Phe Gln Pro Gly Gln Lys
65                  70                  75                  80 gtt tat gtg tgg tac ggg ggt caa gag tgc aca gga ctg gtg gag cag     288
Val Tyr Val Trp Tyr Gly Gly Gln Glu Cys Thr Gly Leu Val Glu Gln
                85                  90                  95 cac agc tgg atg gag ggt cag gtg acc gtc tgg ctg ctg gag cag aag     336
His Ser Trp Met Glu Gly Gln Val Thr Val Trp Leu Leu Glu Gln Lys
            100                 105                 110 ctg cag gtc tgc tgc agg gtg gag gag gtg tgg ctg gca gag ctg cag     384
Leu Gln Val Cys Cys Arg Val Glu Glu Val Trp Leu Ala Glu Leu Gln
        115                 120                 125 ggc ccc tgt ccc cag gca cca ccc ctg gag ccc gga gcc cag gcc ctg     432
Gly Pro Cys Pro Gln Ala Pro Pro Leu Glu Pro Gly Ala Gln Ala Leu
    130                 135                 140 gcc tac agg ccc gtc tcc agg aac atc gat gtc cca aag agg aag tcg     480
Ala Tyr Arg Pro Val Ser Arg Asn Ile Asp Val Pro Lys Arg Lys Ser
145                 150                 155                 160 gac gca gtg gaa atg gat gag atg atg gcg gcc atg gtg ctg acg tcc     528
Asp Ala Val Glu Met Asp Glu Met Met Ala Ala Met Val Leu Thr Ser
                165                 170                 175 ctg tcc tgc agc cct gtt gta cag agt cct ccc ggg acc gag gcc aac     576
Leu Ser Cys Ser Pro Val Val Gln Ser Pro Pro Gly Thr Glu Ala Asn
            180                 185                 190 ttc tct gct tcc cgt gcg gcc tgc gac cca tgg aag gag agt ggt gac     624
Phe Ser Ala Ser Arg Ala Ala Cys Asp Pro Trp Lys Glu Ser Gly Asp
        195                 200                 205 atc tcg gac agc ggc agc agc act acc agc ggt cac tgg agt ggg agc     672
Ile Ser Asp Ser Gly Ser Ser Thr Thr Ser Gly His Trp Ser Gly Ser
    210                 215                 220 agt ggt gtc tcc acc ccc tcg ccc ccc cac ccc cag gcc agc ccc aag     720
Ser Gly Val Ser Thr Pro Ser Pro Pro His Pro Gln Ala Ser Pro Lys
225                 230                 235                 240 tat ttg ggg gat gct ttt ggt tct ccc caa act gat cat ggc ttt gag     768
Tyr Leu Gly Asp Ala Phe Gly Ser Pro Gln Thr Asp His Gly Phe Glu
                245                 250                 255 acc gat cct gac cct ttc ctg ctg gac gaa cca gct cca cga aaa aga     816
Thr Asp Pro Asp Pro Phe Leu Leu Asp Glu Pro Ala Pro Arg Lys Arg
            260                 265                 270 aag aac tct gtg aag gtg atg tac aag tgc ctg tgg cca aac tgt ggc     864
Lys Asn Ser Val Lys Val Met Tyr Lys Cys Leu Trp Pro Asn Cys Gly
        275                 280                 285
```

```
aaa gtt ctg cgc tcc att gtg ggc atc aaa cga cac gtc aaa gcc ctc      912
Lys Val Leu Arg Ser Ile Val Gly Ile Lys Arg His Val Lys Ala Leu
    290                 295                 300 cat ctg ggg gac aca gtg gac tct gat cag ttc aag cgg gag gag gat      960
His Leu Gly Asp Thr Val Asp Ser Asp Gln Phe Lys Arg Glu Glu Asp
305                 310                 315                 320 ttc tac tac aca gag gtg cag ctg aag gag gaa tct gct gct gct gct     1008
Phe Tyr Tyr Thr Glu Val Gln Leu Lys Glu Glu Ser Ala Ala Ala Ala
                325                 330                 335 gct gct gct gcc gca ggc acc cca gtc cct ggg act ccc acc tcc gag     1056
Ala Ala Ala Ala Ala Gly Thr Pro Val Pro Gly Thr Pro Thr Ser Glu
            340                 345                 350 cca gct ccc acc ccc agc atg act ggc ctg cct ctg tct gct ctt cca     1104
Pro Ala Pro Thr Pro Ser Met Thr Gly Leu Pro Leu Ser Ala Leu Pro
        355                 360                 365 cca cct ctg cac aaa gcc cag tcc tcc ggc cca gaa cat cct ggc ccg     1152
Pro Pro Leu His Lys Ala Gln Ser Ser Gly Pro Glu His Pro Gly Pro
    370                 375                 380 gag tcc tcc ctg ccc tca ggg gct ctc agc aag tca gct cct ggg tcc     1200
Glu Ser Ser Leu Pro Ser Gly Ala Leu Ser Lys Ser Ala Pro Gly Ser
385                 390                 395                 400 ttc tgg cac att cag gca gat cat gca tac cag gct ctg cca tcc ttc     1248
Phe Trp His Ile Gln Ala Asp His Ala Tyr Gln Ala Leu Pro Ser Phe
                405                 410                 415 cag atc cca gtc tca cca cac atc tac acc agt gtc agc tgg gct gct     1296
Gln Ile Pro Val Ser Pro His Ile Tyr Thr Ser Val Ser Trp Ala Ala
            420                 425                 430 gcc ccc tcc gcc gcc tgc tct ctc tct ccg gtc cgg agc cgg tcg cta     1344
Ala Pro Ser Ala Ala Cys Ser Leu Ser Pro Val Arg Ser Arg Ser Leu
        435                 440                 445 agc ttc agc gag ccc cag cag cca gca cct gcg atg aaa tct cat ctg     1392
Ser Phe Ser Glu Pro Gln Gln Pro Ala Pro Ala Met Lys Ser His Leu
    450                 455                 460 atc gtc act tct cca ccc cgg gcc cag agt ggt gcc agg aaa gcc cga     1440
Ile Val Thr Ser Pro Pro Arg Ala Gln Ser Gly Ala Arg Lys Ala Arg
465                 470                 475                 480 ggg gag gct aag aag tgc cgc aag gtg tat ggc atc gag cac cgg gac     1488
Gly Glu Ala Lys Lys Cys Arg Lys Val Tyr Gly Ile Glu His Arg Asp
                485                 490                 495 cag tgg tgc acg gcg tgc cgg tgg aag aag gcc tgc cag cgc ttt ctg     1536
Gln Trp Cys Thr Ala Cys Arg Trp Lys Lys Ala Cys Gln Arg Phe Leu
            500                 505                 510 gac                                                                  1539
Asp

<210> SEQ ID NO 2
<211> LENGTH: 513
<212> TYPE: PRT
<213> ORGANISM: Homo sapiens

<400> SEQUENCE: 2

Met Ala Ser Val Leu Ser Arg Arg Leu Gly Lys Arg Ser Leu Leu Gly
1               5                   10                  15

Ala Arg Val Leu Gly Pro Ser Ala Ser Glu Gly Pro Ser Ala Ala Pro
                20                  25                  30

Pro Ser Glu Pro Leu Leu Glu Gly Ala Ala Pro Gln Pro Phe Thr Thr
            35                  40                  45

Ser Asp Asp Thr Pro Cys Gln Glu Gln Pro Lys Glu Val Leu Lys Ala
        50                  55                  60
```

-continued

```
Pro Ser Thr Ser Gly Leu Gln Gln Val Ala Phe Gln Pro Gly Gln Lys
 65                  70                  75                  80

Val Tyr Val Trp Tyr Gly Gly Gln Glu Cys Thr Gly Leu Val Glu Gln
                 85                  90                  95

His Ser Trp Met Glu Gly Gln Val Thr Val Trp Leu Leu Glu Gln Lys
            100                 105                 110

Leu Gln Val Cys Cys Arg Val Glu Glu Val Trp Leu Ala Glu Leu Gln
                115                 120                 125

Gly Pro Cys Pro Gln Ala Pro Pro Leu Glu Pro Gly Ala Gln Ala Leu
            130                 135                 140

Ala Tyr Arg Pro Val Ser Arg Asn Ile Asp Val Pro Lys Arg Lys Ser
145                 150                 155                 160

Asp Ala Val Glu Met Asp Glu Met Met Ala Ala Met Val Leu Thr Ser
                165                 170                 175

Leu Ser Cys Ser Pro Val Val Gln Ser Pro Gly Thr Glu Ala Asn
                180                 185                 190

Phe Ser Ala Ser Arg Ala Ala Cys Asp Pro Trp Lys Glu Ser Gly Asp
            195                 200                 205

Ile Ser Asp Ser Gly Ser Ser Thr Thr Ser Gly His Trp Ser Gly Ser
210                 215                 220

Ser Gly Val Ser Thr Pro Ser Pro Pro His Pro Gln Ala Ser Pro Lys
225                 230                 235                 240

Tyr Leu Gly Asp Ala Phe Gly Ser Pro Gln Thr Asp His Gly Phe Glu
                245                 250                 255

Thr Asp Pro Asp Pro Phe Leu Leu Asp Glu Pro Ala Pro Arg Lys Arg
            260                 265                 270

Lys Asn Ser Val Lys Val Met Tyr Lys Cys Leu Trp Pro Asn Cys Gly
        275                 280                 285

Lys Val Leu Arg Ser Ile Val Gly Ile Lys Arg His Val Lys Ala Leu
        290                 295                 300

His Leu Gly Asp Thr Val Asp Ser Asp Gln Phe Lys Arg Glu Glu Asp
305                 310                 315                 320

Phe Tyr Tyr Thr Glu Val Gln Leu Lys Glu Ser Ala Ala Ala Ala
                325                 330                 335

Ala Ala Ala Ala Ala Gly Thr Pro Val Pro Gly Thr Pro Thr Ser Glu
            340                 345                 350

Pro Ala Pro Thr Pro Ser Met Thr Gly Leu Pro Leu Ser Ala Leu Pro
        355                 360                 365

Pro Pro Leu His Lys Ala Gln Ser Ser Gly Pro Glu His Pro Gly Pro
        370                 375                 380

Glu Ser Ser Leu Pro Ser Gly Ala Leu Ser Lys Ser Ala Pro Gly Ser
385                 390                 395                 400

Phe Trp His Ile Gln Ala Asp His Ala Tyr Gln Ala Leu Pro Ser Phe
                405                 410                 415

Gln Ile Pro Val Ser Pro His Ile Tyr Thr Ser Val Ser Trp Ala Ala
            420                 425                 430

Ala Pro Ser Ala Ala Cys Ser Leu Ser Pro Val Arg Ser Arg Ser Leu
        435                 440                 445

Ser Phe Ser Glu Pro Gln Gln Pro Ala Pro Met Lys Ser His Leu
        450                 455                 460

Ile Val Thr Ser Pro Pro Arg Ala Gln Ser Gly Ala Arg Lys Ala Arg
465                 470                 475                 480
```

-continued

```
Gly Glu Ala Lys Lys Cys Arg Lys Val Tyr Gly Ile Glu His Arg Asp
            485                 490                 495
Gln Trp Cys Thr Ala Cys Arg Trp Lys Lys Ala Cys Gln Arg Phe Leu
        500                 505                 510
Asp

<210> SEQ ID NO 3
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 3
gctctgccat ccttccagat cccagtc                                         27

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ala Leu Pro Ser Phe Gln Ile Pro Val
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Gly Ile Leu Gly Phe Val Phe Thr Leu
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Arg Gly Tyr Val Tyr Gln Gly Leu
1               5
```